United States Patent
Yano et al.

(10) Patent No.: US 10,870,667 B2
(45) Date of Patent: Dec. 22, 2020

(54) ALKYLDIPHENYLMETHANE PROTECTIVE AGENT

(71) Applicant: SEKISUI MEDICAL CO., LTD., Chuo-ku (JP)

(72) Inventors: Shinya Yano, Chuo-ku (JP); Kenta Saito, Chuo-ku (JP); Hideki Kubota, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 0 days.

(21) Appl. No.: 16/757,645

(22) PCT Filed: Nov. 27, 2018

(86) PCT No.: PCT/JP2018/043565
§ 371 (c)(1),
(2) Date: Apr. 20, 2020

(87) PCT Pub. No.: WO2019/123994
PCT Pub. Date: Jun. 27, 2019

(65) Prior Publication Data
US 2020/0325163 A1 Oct. 15, 2020

(30) Foreign Application Priority Data

Dec. 19, 2017 (JP) .................. 2017-242990
May 15, 2018 (JP) .................. 2018-093640

(51) Int. Cl.
*C07F 7/18* (2006.01)
*C07B 63/04* (2006.01)
(Continued)

(52) U.S. Cl.
CPC ............ *C07F 7/1804* (2013.01); *C07B 63/04* (2013.01); *C07C 43/23* (2013.01); *C07C 211/27* (2013.01); *C07C 265/08* (2013.01)

(58) Field of Classification Search
CPC ....... C07F 7/1804; C07B 63/04; C07C 43/23; C07C 211/27; C07C 265/08
See application file for complete search history.

(56) References Cited

U.S. PATENT DOCUMENTS 5,874,532 A 2/1999 Pieken et al.
6,001,966 A * 12/1999 Pieken ................ B01J 19/0046
530/300

(Continued)

FOREIGN PATENT DOCUMENTS

EP 1 510 522 A1 3/2005
JP 2000-500740 A 1/2000
(Continued)

OTHER PUBLICATIONS

M. Lashley et al., 10 Bioorganic & Medicinal Chemistry, 4075-4082 (2002) (Year: 2002).*

(Continued)

*Primary Examiner* — Alexander R Pagano
(74) *Attorney, Agent, or Firm* — Oblon, McClelland, Maier & Neustadt, L.L.P.

(57) ABSTRACT

Provided is an alkyldiphenylmethane protective agent, which can prevent solidification or insolubilization of a compound by protecting a functional group of the compound to achieve easy separation and purification after a reaction. An alkyldiphenylmethane compound represented by general formula (1):

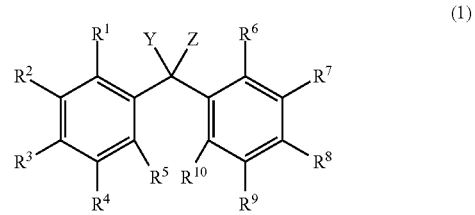

(1)

wherein Y represents —$OR^{19}$ (wherein $R^{19}$ represents a hydrogen atom or an active ester-type protecting group), $NHR^{20}$ (wherein $R^{20}$ represents a hydrogen atom, a $C_{1-6}$ linear or branched alkyl group, or an aralkyl group), isocyanate group, an azide group, or a halogen atom, Z represents a $C_{1-4}$ linear or branched alkyl group, an alkenyl group, or a cycloalkyl group, at least one of $R^1$ to $R^{10}$ represents a group represented by formula (2):

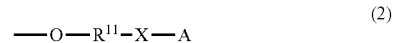

(2)

and the others each independently represent a hydrogen atom, a halogen atom, a alkyl group, or a $C_{1-4}$ alkoxy group; $R^{11}$ represents a $C_{1-16}$ linear or branched alkylene group; X represents O or $CONR^{21}$ (wherein $R^{21}$ represents a hydrogen atom or a $C_{1-4}$ alkyl group); and A represents, for example, a group represented by formula (3):

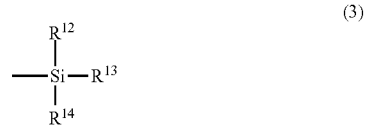

(3)

wherein $R^{12}$, $R^{13}$, and $R^{14}$ may be the same or different and each independently represent a $C_{1-6}$ linear or branched alkyl group or an optionally substituted aryl group; $R^{15}$ represents a single bond or a $C_{1-3}$ linear or (Continued)

branched alkylene group; and $R^{16}$, $R^{17}$, and $R^{18}$ each independently represent a $C_{1-3}$ linear or branched alkylene group.

10 Claims, No Drawings

(51) Int. Cl.
*C07C 43/23* (2006.01)
*C07C 211/27* (2006.01)
*C07C 265/08* (2006.01)

(56) References Cited

U.S. PATENT DOCUMENTS

| | | | |
|---|---|---|---|
| 6,262,251 | B1 | 7/2001 | Pieken et al. |
| 6,737,236 | B1 | 5/2004 | Pieken et al. |
| 9,212,130 | B2 * | 12/2015 | Kai ................. C07D 217/24 |
| 10,508,124 | B2 * | 12/2019 | Yano ................. C07K 1/064 |
| 2003/0215801 | A1 | 11/2003 | Pieken et al. |
| 2004/0116685 | A1 | 6/2004 | Pieken et al. |
| 2005/0048496 | A1 | 3/2005 | Dellinger et al. |
| 2010/0249374 | A1 | 9/2010 | Takahashi |
| 2012/0059149 | A1 | 3/2012 | Takahashi |
| 2014/0005359 | A1 | 1/2014 | Takahashi |
| 2014/0213761 | A1 | 7/2014 | Takahashi |
| 2016/0060198 | A1 | 3/2016 | Takahashi |
| 2017/0008922 | A1 | 1/2017 | Takahashi |
| 2018/0215782 | A1 | 8/2018 | Kono et al. |
| 2019/0023726 | A1 * | 1/2019 | Yano ................. C07B 51/00 |
| 2019/0225631 | A1 * | 7/2019 | Yano ................. C07B 51/00 |
| 2019/0263842 | A1 * | 8/2019 | Yano ................. C07K 1/062 |
| 2019/0308997 | A1 * | 10/2019 | Yano ................. C07F 7/18 |

FOREIGN PATENT DOCUMENTS

| | | |
|---|---|---|
| WO | WO 97/14706 A1 | 4/1997 |
| WO | WO 2010/113939 A1 | 10/2010 |
| WO | WO 2012/029794 A1 | 3/2012 |
| WO | WO 2016/140232 A1 | 9/2016 |
| WO | WO 2017/038650 A1 | 3/2017 |
| WO | WO 2017/221889 A1 | 12/2017 |
| WO | WO 2018/021233 A1 | 2/2018 |
| WO | WO 2018/088527 A1 | 5/2018 |
| WO | WO 2018/155669 A1 | 8/2018 |

OTHER PUBLICATIONS

International Search Report dated Feb. 5, 2019 in PCT/JP2018/043565 filed on Nov. 27, 2018, citing documents AA-AD, AF, AH-AL, AO-AV, and AAO-AAP therein, 2 pages.

* cited by examiner

ALKYLDIPHENYLMETHANE PROTECTIVE AGENT

FIELD OF THE INVENTION

The present invention relates to an alkyldiphenylmethane compound useful as a protective agent for a carboxy group, a hydroxy group, an amino group, an amide group, a mercapto group, or the like.

BACKGROUND OF THE INVENTION

In synthesis of peptides or various compounds, protection of functional groups such as a carboxy group, a hydroxy group, an amino group, an amide group, and a mercapto group may be required for carrying out the reaction. Desirable protecting groups include those which can protect functional groups by an easy process and can be eliminated under moderate conditions. For example, benzyl esters (Bn) and tert-butyl ester are known as examples of a protecting group for a carboxy group. Recently, it is reported that benzyl alcohol-based compounds and diphenylmethane-based compounds are useful as protecting groups (Patent Literatures 1 to 3).

CITATION LIST

Patent Literatures

Patent Literature 1: WO 2012/029794 A
Patent Literature 2: WO 2010/113939 A
Patent Literature 3: WO 2017/038650 A

SUMMARY OF THE INVENTION

Problem to be Solved by the Invention

There is a drawback that a compound in which a functional group is protected with a conventional protecting group can easily be precipitated. Specifically, in peptide synthesis, since such a compound becomes insoluble even in an organic solvent, a reaction or separation and purification of the compound after the reaction often become difficult. These difficulties in separation and purification are serious problems in peptide synthesis in which condensation reactions are carried out successively.

Under such circumstances, Patent Literature 3 provides a benzyl compound as a protective group for a carboxy group, which protects a functional group of a compound, which leads to dissolution of the compound in an organic solvent without solidification or insolubilization, which allows easy separation and purification of the compound after a reaction.

Meanwhile, in synthesis of peptides in which a carboxy terminal or a side chain is a carboxamide group, a synthesis method including protecting the carboxamide group by a diphenylmethane compound has been widely used. However, it is difficult to develop a protective group which provides high solubility based on a diphenylmethane-based compound.

Accordingly, an object of the present invention is to provide a diphenylmethane protective agent, which protects a functional group of a compound, which leads to dissolution of the compound in an organic solvent without solidification or insolubilization, which allows easy separation and purification of the compound after a reaction.

Means for Solving the Problem

The present inventors have made investigations on various substituents on phenyl groups of an alkyldiphenylmethane compound which has an aliphatic substituent on its methylene portion. As a result, they have found that a compound in which a functional group is protected with an alkyldiphenylmethane compound substituted with an alkyloxy group having a silyl group at the end is hardly precipitated in an organic solvent and easily separated and purified by a liquid-liquid phase separation operation, and thus the compound is useful as a protective agent for a carboxyamide group, and consequently have made the present invention.

That is, the present invention provides the following [1] to [8].

[1] An alkyldiphenylmethane compound represented by general formula (1):

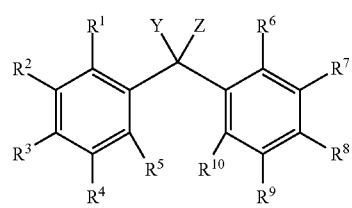

(1)

wherein Y represents $-OR^{19}$ (wherein $R^{19}$ represents a hydrogen atom or an active ester-type protecting group), $NHR^{20}$ (wherein $R^{20}$ represents a hydrogen atom, a $C_{1-6}$ linear or branched alkyl group, or an aralkyl group), an isocyanate group, an azide group, or a halogen atom, Z represents a $C_{1-4}$ linear or branched alkyl group, an alkenyl group, or a cycloalkyl group, at least one of $R^1$ to $R^{10}$ represents a group represented by formula (2):

(2)

and the others each independently represent a hydrogen atom, a halogen atom, a $C_{1-4}$ alkyl group, or a $C_{1-4}$ alkoxy group; $R^{11}$ represents a $C_{1-16}$ linear or branched alkylene group; X represents O or $CONR^{21}$ (wherein $R^{21}$ represents a hydrogen atom or a $C_{1-4}$ alkyl group); and A represents a group represented by formula (3), (4), (5), (6), (7), (8), (9), (10), (11), (12), or (13):

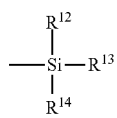

(3)

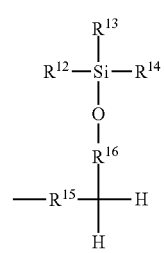

(4)

-continued (5)
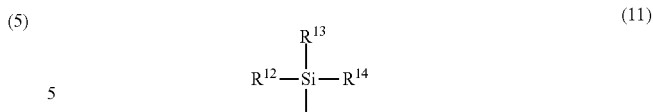

(6)
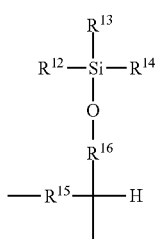

(7)
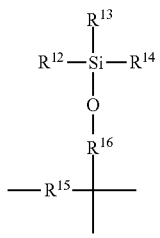

(8)
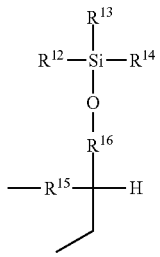

(9)
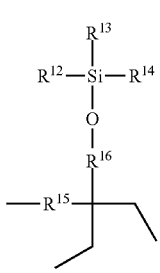

(10)
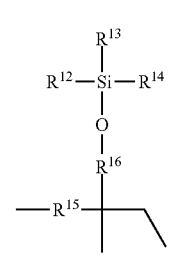

(11)
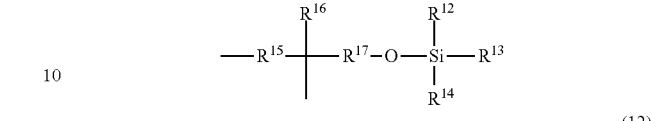

(12)
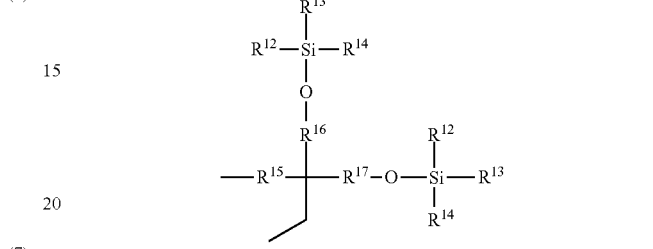

(13)
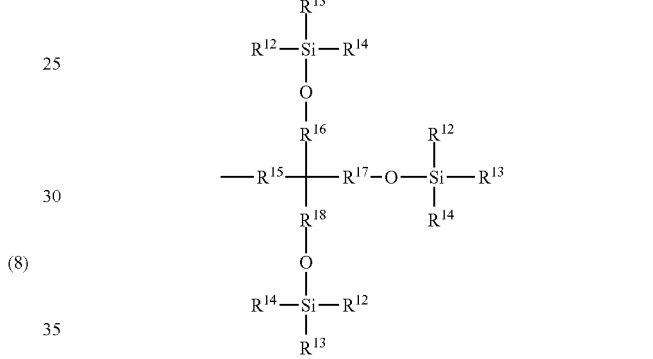

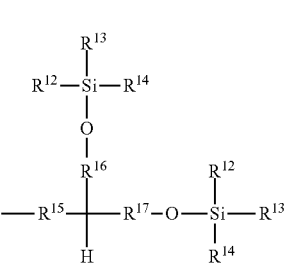

wherein $R^{12}$, $R^{13}$, and $R^{14}$ may be the same or different and each independently represent a 01-6 linear or branched alkyl group or an optionally substituted aryl group; $R^{15}$ represents a single bond or a $C_{1-3}$ linear or branched alkylene group, and $R^{16}$, $R^{17}$, and $R^{18}$ each independently represent a $C_{1-3}$ linear or branched alkylene group.

[2] The alkyldiphenylmethane compound according to [1], wherein Y is —$OR^{19}$ (wherein $R^{19}$ represents a hydrogen atom), —$NHR^{20}$ (wherein $R^{20}$ represents a hydrogen atom, a $C_{1-6}$ linear or branched alkyl group, or an aralkyl group), or an isocyanate group.

[3] The alkyldiphenylmethane compound according to [1] or [2], wherein Z is a $C_{1-4}$ linear or branched alkyl group.

[4] The alkyldiphenylmethane compound according to any one of [1] to [3], wherein at least one of $R^1$ to $R^5$ and at least one of $R^6$ to $R^{10}$ are each independently a group represented by formula (2) and the others are each independently a hydrogen atom, a $C_{1-4}$ alkyl group, or a $C_{1-4}$ alkoxy group.

[5] The alkyldiphenylmethane compound according to any one of [1] to [4], wherein $R^{11}$ is a $C_{2-16}$ linear or branched alkylene group.

[6] The alkyldiphenylmethane compound according to any one of [1] to [5], wherein $R^{11}$ is a $C_{6-16}$ linear or branched alkylene group.

[7] The alkyldiphenylmethane compound according to any one of [1] to [6], wherein $R^{15}$ is a single bond or a methylene group, and $R^{16}$, $R^{17}$, and $R^{18}$ are each independently a methylene group.

[8] A protective agent for a carboxy group, a hydroxy group, an amino group, an amide group, or a mercapto group, comprising an alkyldiphenylmethane compound according to any one of [1] to [7].

Effects of the Invention

A compound in which a functional group is protected by an alkyldiphenylmethane compound (1) of the present invention readily becomes liquid and has an increased solubility in a solvent, which leads to easy separation and purification after a reaction.

If insolubilization or solidification of raw materials or intermediates is an obstacle in a process of producing various chemicals such as medicines and agrochemicals, such problems can be solved by bonding the alkyldiphenylmethane compound (1) of the present invention to the raw materials or the intermediate compounds to increase liquidity and solubility thereof.

DESCRIPTION OF THE EMBODIMENTS

An alkyldiphenylmethane compound of the present invention represented by general formula (1) is characterized in that at least one of $R^1$ to $R^{10}$ has a structure represented by formula (2). Such a structure facilitates liquefaction of a compound protected with the alkyldiphenylmethane compound (1) and significantly increases solubility in a solvent.

In general formula (1), Y represents —$OR^{19}$ (wherein $R^{19}$ represents a hydrogen atom or an active ester-type protecting group), —$NHR^{20}$ (wherein $R^{20}$ represents a hydrogen atom, a $C_{1-6}$ linear or branched alkyl group, or an aralkyl group), isocyanate group, an azide group, or a halogen atom. Examples of the halogen atom include a fluorine atom, a bromine atom, a chlorine atom, and an iodine atom.

Examples of the active ester-type protecting group include an active ester-type carbonyl group and an active ester-type sulfonyl group. Examples of the active ester-type carbonyl group include a carbonyloxy succinimide, an alkoxycarbonyl group, an aryloxycarbonyl group, and an aralkyloxy carbonyl group, and more preferred is, for example, a carbonyloxy succinimide.

Examples of the active ester-type sulfonyl group include an alkylsulfonyl group and an arylsulfonyl group, and more preferred are, for example, a $C_1$-$C_6$ alkylsulfonyl group and a p-toluenesulfonyl group.

Y is preferably —$OR^{19}$ (wherein $R^{19}$ represents a hydrogen atom), —$NHR^{20}$ (wherein $R^{20}$ represents a hydrogen atom, a $C_{1-6}$ linear or branched alkyl group, or an aralkyl group), or an isocyanate group.

Z represents a $C_{1-4}$ linear or branched alkyl group, an alkenyl group, or a cycloalkyl group. Examples of the $C_{1-4}$ alkyl group include a methyl group, an ethyl group, an n-propyl group, an isopropyl group, an n-butyl group, an isobutyl group, a sec-butyl group, and a tert-butyl group. Inter alia, preferred is a $C_{1-4}$ alkyl group, and more preferred is a methyl group.

Examples of the alkenyl group include a $C_{2-4}$ alkenyl group such as an ethenyl group, a 1-propenyl group, a 2-propenyl group, an isopropenyl group, and a 3-butenyl group. Inter alia, preferred is an isopropenyl group.

As the cycloalkyl group, preferred is a $C_{3-6}$ cycloalkyl group, and examples thereof include a cyclopropyl group, a cyclobutyl group, a cyclopentyl group, and a cyclohexyl group. Inter alia, preferred are a cyclobutyl group and a cyclohexyl group.

The alkyldiphenylmethane compound of the present invention refers to a group in which at least one of $R^1$ to $R^{10}$ is represented by formula (2). Inter alia, preferred is a group in which 1 to 4 of $R^1$ to $R^{10}$ are represented by formula (2), more preferred is a group in which 2 of $R^1$ to $R^{10}$ are represented by formula (2).

The others are each independently a hydrogen atom, a halogen atom, a $C_{1-4}$ alkyl group, or a $C_{1-4}$ alkoxy group. Examples of the other halogen atoms represented by $R^1$ to $R^{10}$ include a fluorine atom, a chlorine atom, and a bromine atom. Inter alia, preferred is a chlorine atom. Examples of the other $C_{1-4}$ alkoxy group include a methoxy group, an ethoxy group, an n-propyloxy group, an isopropyloxy group, and an n-butyloxy group. Inter alia, preferred are a methoxy group and an ethoxy group. Examples of the $C_{1-4}$ alkyl group include a methyl group, an ethyl group, an n-propyl group, an isopropyl group, and an n-butyl group. Inter alia, preferred are a methyl group and an ethyl group.

More preferred is a group in which at least one of $R^1$ to $R^5$ and at least one of $R^6$ to $R^{10}$ are each independently a group represented by formula (2) and the others are each independently a hydrogen atom, a $C_{1-4}$ alkyl group, or a $C_{1-4}$ alkoxy group. Even more preferred is a group in which 1 to 3 of $R^1$ to $R^5$ and 1 to 3 of $R^6$ to $R^{10}$ are each independently a group represented by formula (2) and the others are each independently a hydrogen atom, a $C_{1-4}$ alkyl group, or a $C_{1-4}$ alkoxy group.

$R^{11}$ represents a $C_{1-16}$ linear or branched alkylene group. The alkylene group is preferably a $C_{6-16}$ linear or branched alkylene group, more preferably a $C_{6-16}$ linear or branched alkylene group, and even more preferably a $C_{8-14}$ linear or branched alkylene group. Specific examples of the alkylene group include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, and a tetradecamethylene group.

X represents O or $CONR^{21}$.

Herein, $R^{21}$ represents a hydrogen atom or a $C_{1-4}$ alkyl group, and is preferably a hydrogen atom.

X is preferably O or CONH.

The letter A represents a group represented by formula (3), (4), (5), (6), (7), (8), (9), (10), (11), (12), or (13). $R^{12}$, $R^{13}$, and $R^{14}$ may be the same or different and each independently represent a $C_{1-6}$ linear or branched alkyl group or an optionally substituted aryl group. Herein, examples of the $C_{1-6}$ alkyl group include a methyl group, an ethyl group, an n-propyl group, an isopropyl group, an n-butyl group, an isobutyl group, a sec-butyl group, a tert-butyl group, an n-pentyl group, and an n-hexyl group. Inter alia, preferred is a $C_{1-4}$ alkyl group, and more preferred are a methyl group, tert-butyl group, and an isopropyl group.

Examples of the optionally substituted aryl group include a $C_{6-10}$ aryl group. Specific examples include a phenyl group and a naphthyl group, each optionally substituted with a $C_{1-3}$ alkyl group. Inter alia, more preferred is a phenyl group.

$R^{15}$ represents a single bond or a $C_{1-3}$ linear or branched alkylene group. Examples of the $C_{1-3}$ linear or branched alkylene group include a methylene group, an ethylene group, a trimethylene group, and a propylene group. As $R^{15}$, preferred is a single bond.

$R^{16}$, $R^{17}$, and $R^{18}$ each independently represent a $C_{1-3}$ linear or branched alkylene group. Examples of the $C_{1-3}$ linear or branched alkylene group include a methylene group, an ethylene group, a trimethylene group, and a propylene group. Inter alia, preferred is a methylene group.

More preferably, $R^{15}$ is a single bond or a methylene group, and $R^{16}$, $R^{17}$, and $R^{18}$ are each independently a methylene group.

Even more preferred is a compound represented by general formula (1) in which Y is $-OR^{19}$ (wherein $R^{19}$ represents a hydrogen atom) or $-NHR^{20}$ (wherein $R^{20}$ represents a hydrogen atom, a $C_{1-6}$ linear or branched alkyl group, or an aralkyl group); Z is a $C_{1-4}$ linear or branched alkyl group; at least one, and preferably 1 to 3, of $R^1$ to $R^5$ is a group represented by formula (2), at least one, and preferably 1 to 3, of $R^6$ to $R^{10}$ is a group represented by formula (2), and the others are each independently a hydrogen atom, a $C_{1-4}$ alkyl group, or a $C_{1-4}$ alkoxy group; $R^{11}$ is a $C_{2-16}$ linear or branched alkylene group; $R^{15}$ is a single bond or a methylene group; and $R^{16}$, $R^{17}$, and $R^{18}$ are each independently a methylene group.

Still more preferred is a compound in which, in formula (2), $R^{11}$ is a $C_{6-16}$ linear or branched alkyl group; X is O or CONH; A is a group represented by formula (3) or (13); $R^{12}$, $R^{13}$, and $R^{14}$ are the same or different and each independently represent a $C_{1-4}$ alkyl group; $R^{16}$ is a single bond; and $R^{16}$, $R^{17}$, and $R^{18}$ are each independently a methylene group.

Herein, specific examples of those to which a group represented by formula (2) is bonded are shown below.

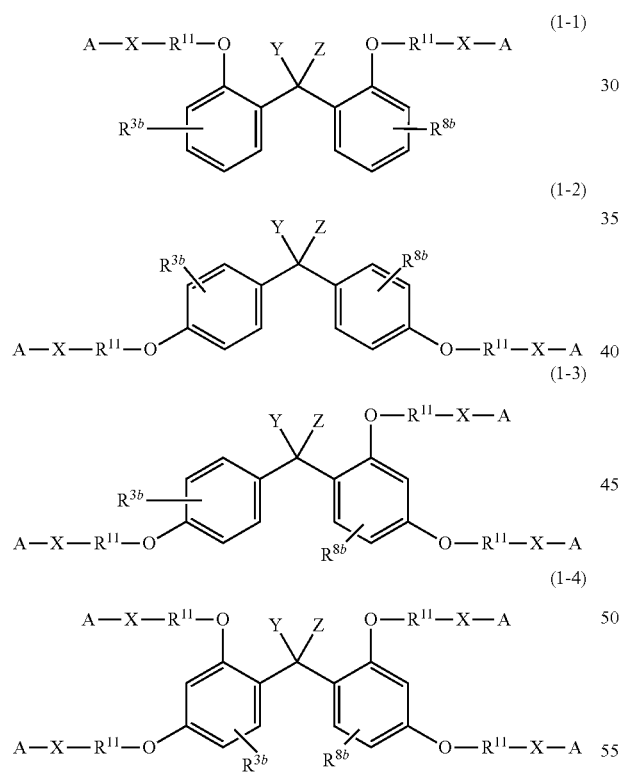

wherein $R^{3b}$ and $R^{8b}$ each independently represent a hydrogen atom, a $C_{1-4}$ alkyl group, or a $C_{1-4}$ alkoxy group, and Y, Z, A, X, and $R^{11}$ are the same as defined above.

Specific examples of the alkyldiphenylmethane compound (1) of the present invention include the following (a) to (f). In (a) to (f), Y represents $-OR^{19}$ (wherein $R^{19}$ represents a hydrogen atom) or $-NHR^{20}$ (wherein $R^{20}$ represents a hydrogen atom, a $C_{1-6}$ linear or branched alkyl group, or an aralkyl group), and Z represent a $C_{1-4}$ linear or branched alkyl group.

(a) TIPS2-Type-PP Protective Agent

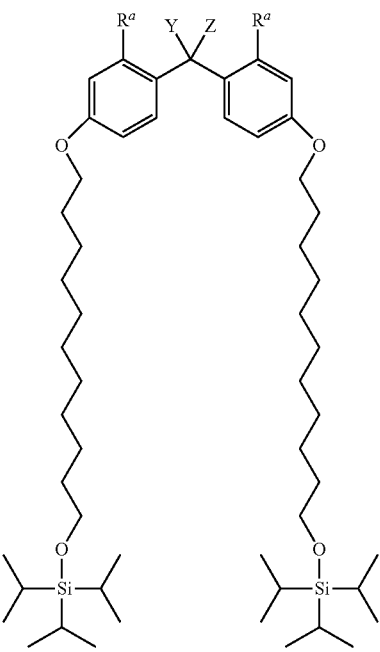

Herein, $R^a$ represents a hydrogen atom, a $C_{1-4}$ alkyl group, or a $C_{1-4}$ alkoxy group, and Y and Z are the same as defined above.

(b) TIPS2-Type-OO Protective Agent

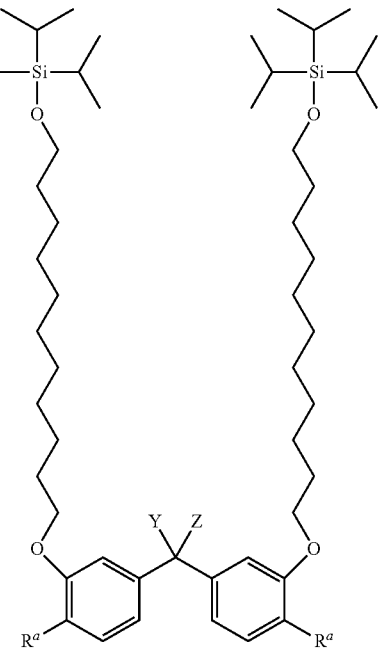

Herein, $R^a$ represents a hydrogen atom, a $C_{1-4}$ alkyl group, or a $C_{1-4}$ alkoxy group, and Y and Z are the same as defined above.

(c) TIPS3-Type-OPP Protective Agent
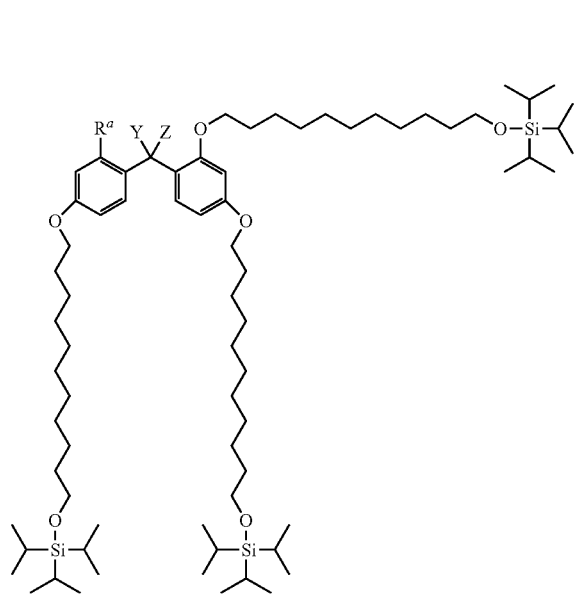
Herein, $R^a$ represents a hydrogen atom, a $C_{1-4}$ alkyl group, or a $C_{1-4}$ alkoxy group, and Y and Z are the same as defined above.
(d) TIPS4-Type-PP Protective Agent
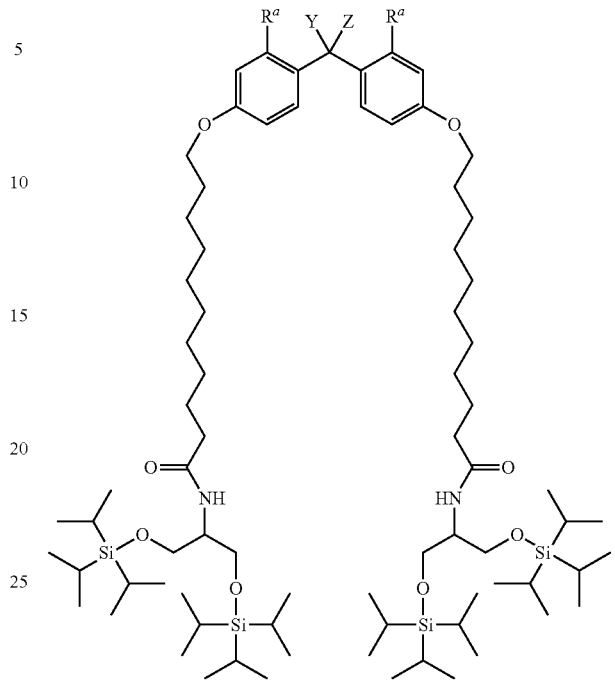
Herein, $R^a$ represents a hydrogen atom, a $C_{1-4}$ alkyl group, or a $C_{1-4}$ alkoxy group, and Y and Z are the same as defined above.
(e) TIPS6-Type-PP Protective Agent
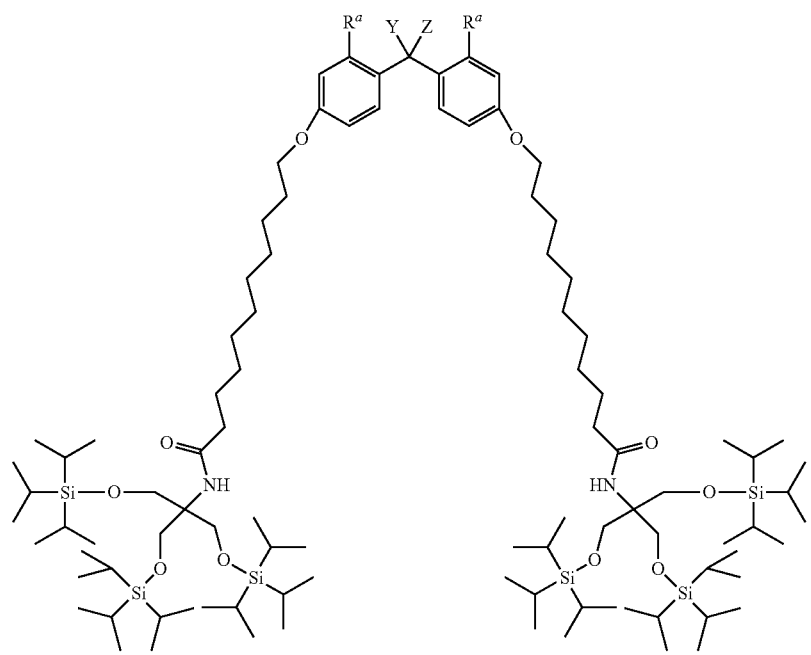

Herein, $R^a$ represents a hydrogen atom, a $C_{1-4}$ alkyl group, or a $C_{1-4}$ alkoxy group, and Y and Z are the same as defined above.

(f) TBDPS2-Type-PP Protective Agent

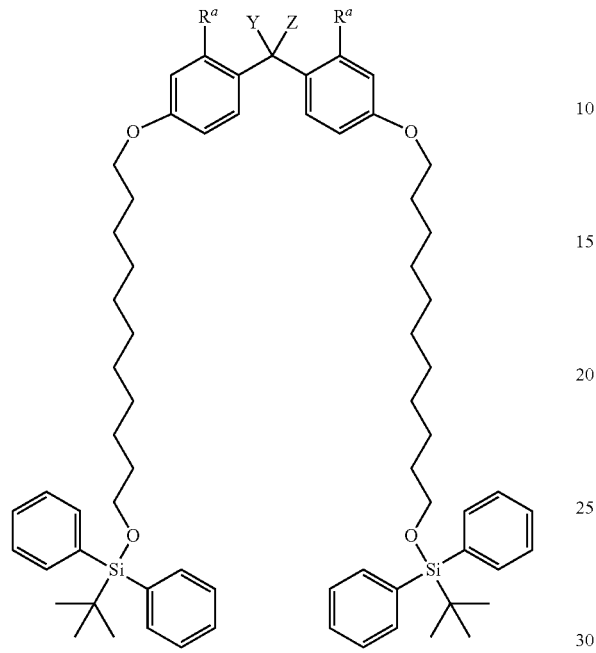

(5)

Herein, $R^a$ represents a hydrogen atom, a $C_{1-4}$ alkyl group, or a $C_{1-4}$ alkoxy group, and Y and Z are the same as defined above.

The alkyldiphenylmethane compound (1) of the present invention can be produced, for example, according to the following reaction scheme.

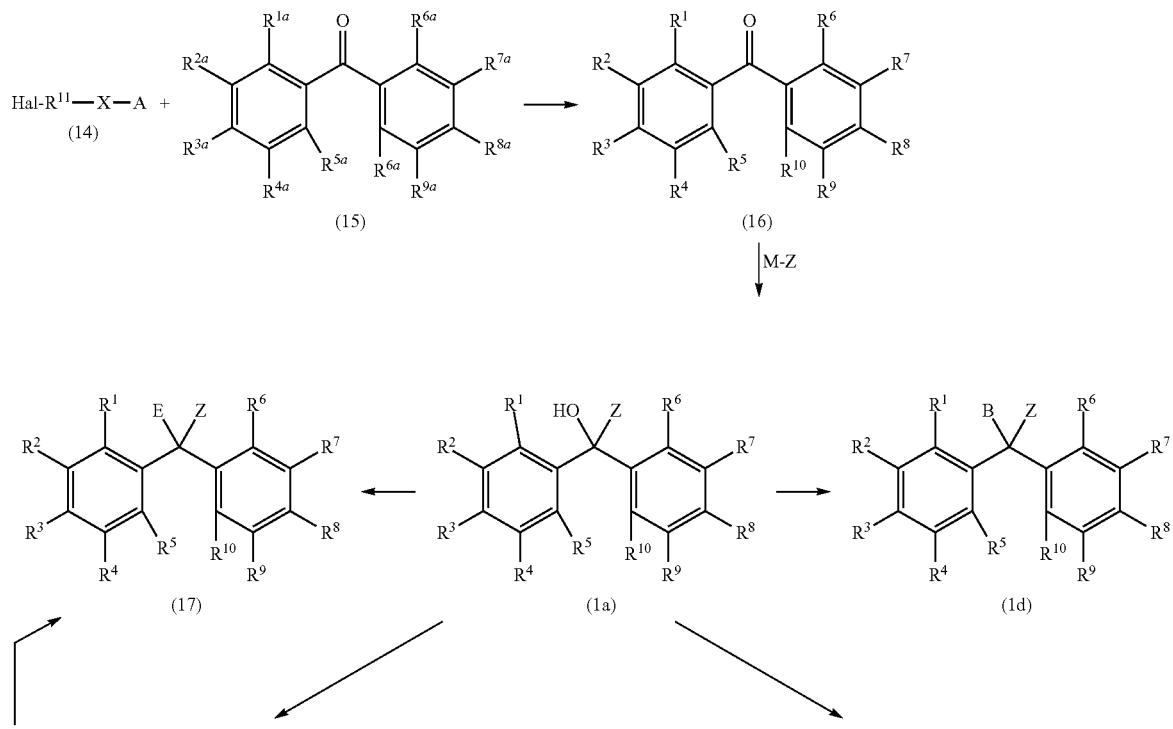

-continued

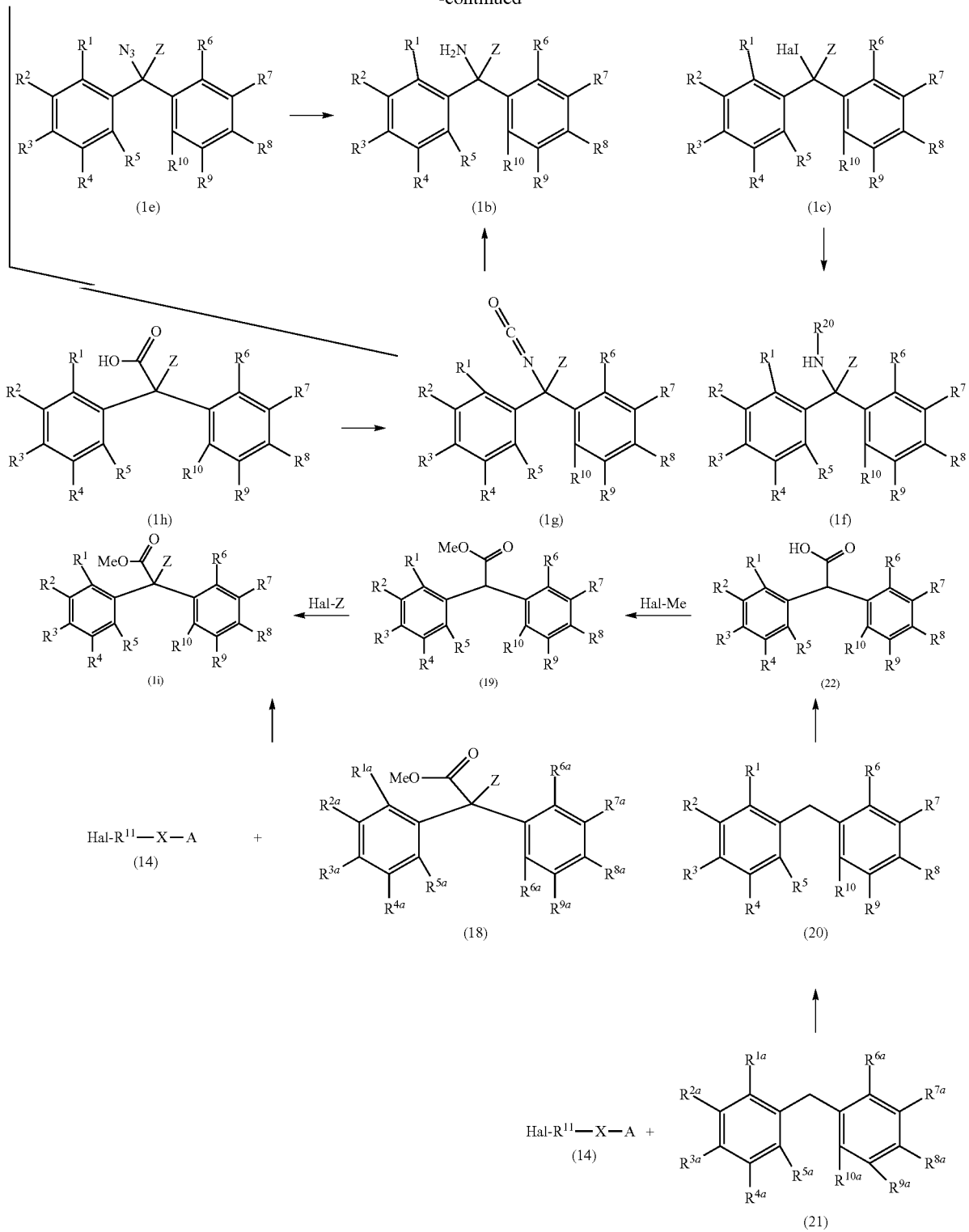

Herein, Hal represents a halogen atom, at least one of $R^{1a}$ to $R^{10a}$ represents a hydroxy group and the others each independently represent a hydrogen atom, a halogen atom, a $C_{1-4}$ alkyl group, or a $C_{1-4}$ alkoxy group, B represents an amino acid having a mercapto group or an amino acid derivative having a mercapto group, E represents a compound having a —CONH— group, M represents MgBr, MgCl, MgI, or Li, and $R^1$ to $R^{10}$, $R^{20}$, X, Z, and A are the same as defined above.

A silyloxylated alkyl halide (14) is reacted with a diphenylketone (15) to give a silyloxy diphenylketone (16), and subsequently the silyloxy diphenylketone (16) is reacted with an organic metal reagent to give a compound (1a). Then, the compound (1a) is azidated to give an azide compound (1e), and the azide group is subjected to Staudinger reaction to afford an alkyldiphenylmethane compound (1b) having an amino group. The alkyldiphenylmethane compound (1a) having a hydroxy group is reacted with a compound having a carboxamide group to afford a compound (17). The alkyldiphenylmethane compound (1a) having a hydroxy group is halogenated to give an alkyldiphenylmethane compound (1c) having a halogen atom, and then the alkyldiphenylmethane compound (1c) is reacted with an amine represented by $R^{20}$—$NH_2$ to afford a compound (1f). The alkyldiphenylmethane compound (1a) having a hydroxy group is reacted with an amino acid having a mercapto group or an amino acid derivative having a mercapto group to afford a compound (1d).

Further, the silyloxylated alkyl halide (14) is reacted with a diphenylmethane derivative (21) to give a silyloxy diphenylmethane (20), the silyloxy diphenylmethane (20) is reacted with carbon dioxide to give a compound (22), and then the compound (22) is reacted with a halogenated methyl for protecting a carboxy group to afford a compound (19). Then, the compound (19) is reacted with a Hal-Z to give an alkyldiphenylmethane compound (1i) having an ester group. Alternatively, the alkyldiphenylmethane compound (1i) is produced by the reaction of the silyloxylated alkyl halide (14) with an alkyldiphenylmethyl ester (18). The ester (1i) is subjected to hydrolysis to give a carboxylic acid (1h), and the carboxylic acid (1h) is subjected to Curtius rearrangement reaction to afford an isocyanate compound (1g) and the alkyldiphenylmethane compound (1b) having an amino group. Meanwhile, the isocyanate compound (1g) is reacted with a compound having a carboxy group to give a compound (17).

The silyloxylated alkyl halide (14) as a raw material can be produced by, for example, reacting a halogenated alcohol with a silylation agent in the presence of a base. Examples of the halogen atom in formula (14) include a bromine atom.

Examples of the silylation agent used in the above reaction include triisopropylsilyl chloride (TIPSCl), triisopropylsilyl bromide, triisopropylsilyl iodide, methanesulfonyl triisopropylsilyl, trifluoromethanesulfonyl isopropylsilyl, p-toluenesulfonyl triisopropylsilyl, tert-butyldiphenylchlorosilane (TBDPSCl), and tert-butyldimethylchlorosilane (TBSCl).

Examples of the base include organic bases such as TEA, DIPEA, DBU, diazabicyclononene (DBN), DABCO, imidazole, N-methyl imidazole, N,N-dimethyl aniline, pyridine, 2,6-lutidine, DMAP, LDA, NaOAc, MeONa, MeOK, lithium hexamethyldisilazide (LHMDS), and sodium bis(trimethylsilyl)amide (NaHMDS); and inorganic bases such as $Na_2CO_3$, $NaHCO_3$, NaH, $NaNH_2$, $K_2CO_3$, and $Cs_2CO_3$.

Examples of the solvent include hydrocarbons such as hexane and heptane; ethers such as diethyl ether, diisopropyl ether, cyclopentyl methyl ether (CPME), tetrahydrofuran, and dioxane; nitriles such as acetonitrile; amides such as dimethylformamide (DMF), dimethylacetamide, and hexamethylphosphoramide; sulfoxides such as dimethylsulfoxide; lactams such as N-methylpyrrolidone; halogenated hydrocarbons such as chloroform and dichloromethane; and aromatic hydrocarbons such as toluene and xylene; or a mixed solvent thereof.

The reaction may be carried out, for example, at 0° C. to 100° C. for 1 to 24 hours.

The reaction between the silyloxylated alkyl halide (14) and the compound (15), (18), or (21) is preferably carried out in the presence of a base.

Examples of the base used in the above reaction include organic bases such as TEA, DIPEA, DBU, DBN, DABCO, imidazole, N-methyl imidazole, N,N-dimethyl aniline, pyridine, 2,6-lutidine, DMAP, LDA, NaOAc, MeONa, MeOK, lithium hexamethyldisilazide (LHMDS), and sodium bis(trimethylsilyl)amide (NaHMDS); and inorganic bases such as $Na_2CO_3$, $NaHCO_3$, NaH, $K_2CO_3$, and $Cs_2CO_3$.

Examples of the solvent include hydrocarbons such as hexane and heptane; ethers such as diethyl ether, diisopropyl ether, CPME, tetrahydrofuran, and dioxane; nitriles such as acetonitrile; amides such as DMF, dimethylacetamide, and hexamethylphosphoramide; sulfoxides such as dimethylsulfoxide; lactams such as N-methylpyrrolidone; halogenated hydrocarbons such as chloroform and dichloromethane; and aromatic hydrocarbons such as toluene and xylene; or a mixed solvent thereof.

The reaction may be carried out, for example, at 40° C. to 150° C. for 1 to 24 hours.

Examples of the method for producing the compound (1a) from the compound (16) include a method comprising allowing the compound (16) to react with an organic metal reagent M-Z.

Examples of the organic metal reagent include a Grignard reagent which can be prepared from a Hal-Z and a lithium reagent. Examples of the solvent include ethers such as diethyl ether, diisopropyl ether, CPME, tetrahydrofuran, and dioxane; aromatic hydrocarbons such as toluene and xylene; and halogenated hydrocarbons such as chloroform and dichloromethane; or a mixed solvent thereof. The reaction is preferably carried out, for example, at −78° C. to 100° C. for 1 to 48 hours.

The method for azidation of the hydroxy group in the compound (1a) is preferably a method comprising allowing the compound (1a) to react with diphenylphosphoryl azide or bis(p-nitrophenyl)phosphoryl azide in the presence of a base.

Examples of the base include organic bases such as DBU, DBN, TEA, DIPEA, and DABCO. Examples of the solvent include hydrocarbons such as hexane and heptane; ethers such as diethyl ether, diisopropyl ether, CPME, tetrahydrofuran, and dioxane; and aromatic hydrocarbons such as toluene and xylene; or a mixed solvent thereof. The reaction may be carried out, for example, at 0° C. to 100° C. for 0.5 to 144 hours.

Examples of the method for reducing the azide compound (1e) to the amine compound (1b) include Staudinger reaction comprising allowing the azide compound (1e) to react with triphenylphosphine in the presence of water or a catalytic reduction. Inter alia, preferred is the Staudinger reaction.

Examples of the solvent for the Staudinger reaction include hydrocarbons such as hexane and heptane; ethers such as diethyl ether, diisopropyl ether, CPME, tetrahydrofuran, and dioxane; and aromatic hydrocarbons such as toluene and xylene; or a mixed solvent thereof. The reaction may be carried out, for example, at 20° C. to 100° C. for 1 to 24 hours.

Examples of the reaction between the compound (1a) and the compound having a carboxamide group include a reaction in the presence of an acid catalyst.

Examples of the compound having a carboxamide group or a —$OCONH_2$ group include Fmoc-$NH_2$, ethyl carbamate, isopropyl carbamate, Ac$NH_2$, HCON$H_2$, Cbz-$NH_2$, $CF_3$CON$H_2$, and Fmoc-amino acid-$NH_2$. Examples of the acid catalyst include acids such as trifluoromethanesulfonic acid, methanesulfonic acid, p-toluene sulfonic acid, acetic acid, hydrochloric acid, and sulfuric acid. Examples of the solvent include hydrocarbons such as hexane and heptane; ethers such as diethyl ether, diisopropyl ether, CPME, tetrahydrofuran, and dioxane; aromatic hydrocarbons such as toluene and xylene; and halogenated hydrocarbons such as chloroform and dichloromethane; or a mixed solvent thereof. The reaction may be carried out, for example, at 20° C. to 150° C. for 0.5 to 48 hours.

The compound (1c) can be produced from the compound (1a), for example, by allowing the compound (1a) to react with a halogenating agent in the presence of a base.

Examples of the halogenating agent include thionyl chloride, acetyl chloride, acetyl bromide, triphenylphosphine/carbon tetrachloride, and triphenylphosphine/carbon tetrachloride.

Examples of the base include organic bases such as pyridine, TEA, DBU, DBN, DIPEA, and DABCO.

Examples of the solvent include hydrocarbons such as hexane and heptane; ethers such as diethyl ether, diisopropyl ether, CPME, tetrahydrofuran, and dioxane; aromatic hydrocarbons such as toluene and xylene; halogenated hydrocarbons such as chloroform and dichloromethane; and dimethylformamide (DMF); or a mixed solvent thereof. The reaction may be carried out, for example, at 0° C. to 100° C. for 0.5 to 24 hours.

The reaction between the compound (1a) and the amino acid derivative having a mercapto group is preferably a method comprising allowing the compound (1a) to react with an amino acid having a mercapto group or an amino acid derivative having a mercapto group in the presence of an acid catalyst.

Examples of the amino acid having a mercapto group include cysteine, homocysteine, mercaptonorvaline, and mercaptonorleucine. Examples of the amino acid derivative having a mercapto group include the above amino acids in which N terminals of the compounds are N-methylated; the above amino acids in which N terminals of the compounds are each protected with, for example, a benzyloxycarbonyl (Cbz or Z) group, a fluorenylmethoxycarbony (Fmoc) group, an acetyl (Ac) group, a benzyl group, an allyl group, an allyloxycarbonyl (Aloc) group, a 2-nitrobenzenesulfonyl (Ns) group, a 2,4-dinitrobenzenesulfonyl (DNs) group, and a 4-nitrobenzenesulfonyl (Nos) group; the above amino acids in which C terminals of the compounds are each protected with, for example, an amide group, a methyl ester group, an ethyl ester group, a tert-butyl ester group, a benzyl ester group, and an allyl ester group; and the above amino acids in which both N terminals and C terminals are each protected with the above protecting groups.

Examples of the acid catalyst include acids such as trifluoromethanesulfonic acid, methanesulfonic acid, p-toluene sulfonic acid, acetic acid, hydrochloric acid, and sulfuric acid. Examples of the solvent include hydrocarbons such as hexane and heptane; ethers such as diethyl ether, diisopropyl ether, CPME, tetrahydrofuran, and dioxane; aromatic hydrocarbons such as toluene and xylene; and halogenated hydrocarbons such as chloroform and dichloromethane; or a mixed solvent thereof. The reaction may be carried out, for example, at 20° C. to 150° C. for 0.5 to 24 hours.

The compound (1f) can be produced from the compound (1c), for example, by allowing the compound (1c) to react with an amine represented by $R^{20}$—$NH_2$ in the presence of a base.

Examples of the base include tertiary amines such as diisopropyl amine and triethyl amine. Examples of the solvent include hydrocarbons such as hexane and heptane; ethers such as diethyl ether, diisopropyl ether, CPME, tetrahydrofuran, and dioxane; aromatic hydrocarbons such as toluene and xylene; and halogenated hydrocarbons such as chloroform and dichloromethane; or a mixed solvent thereof. The reaction may be carried out, for example, at 0° C. to 100° C. for 0.5 to 24 hours.

The compound (22) can be produced from the compound (20), for example, by allowing the compound (20) to react with carbon dioxide in the presence of a base.

Examples of the base include organic bases such as LDA, methyllithium, n-butyllithium, sec-butyllithium, tert-butyllithium, lithium hexamethyldisilazide (LHMDS), and sodium bis(trimethylsilyl)amide (NaHMDS); and inorganic bases such as sodium, potassium, $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; ketones such as acetone and methyl ethyl ketone; amides such as DMF, dimethylacetamide, and hexamethylphosphoramide; sulfoxides such as dimethyl sulfoxide; lactams such as N-methylpyrrolidone; and aromatic hydrocarbons such as benzene; or a mixed solvent thereof. The reaction may be carried out, for example, at −78° C. to 80° C. for 1 to 24 hours.

The compound (19) can be produced from the compound (22), for example, by allowing the compound (22) to react with a halogenated methyl in the presence of a base.

Examples of the base include organic bases such as TEA, DIPEA, DBU, DBN, DABCO, imidazole, N-methyl imidazole, N,N-dimethyl aniline, pyridine, 2,6-lutidine, DMAP, LDA, NaOAc, MeONa, MeOK, lithium hexamethyldisilazide (LHMDS), sodium bis(trimethylsilyl)amide (NaHMDS), and lithium diisopropylamide; and inorganic bases such as LiOH, NaOH, KOH, $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; and aromatic hydrocarbons such as toluene and xylene; or a mixed solvent thereof. The reaction may be carried out, for example, at 0° C. to 100° C. for 1 to 24 hours.

The compound (1i) can be produced from the compound (19), for example, by allowing the compound (19) to react with a Hal-Z in the presence of a base.

Examples of the base include organic bases such as TEA, DIPEA, DBU, DBN, DABCO, imidazole, N-methyl imidazole, N,N-dimethyl aniline, pyridine, 2,6-lutidine, DMAP, LDA, NaOAc, MeONa, MeOK, lithium hexamethyldisilazide (LHMDS), sodium bis(trimethylsilyl)amide (NaHMDS), lithium diisopropylamide, n-butyllithium, sec-butyllithium, and tert-butyllithium; and inorganic bases such as LiOH, NaOH, KOH, $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; and aromatic hydrocarbons such as toluene and xylene; or a mixed solvent thereof. The reaction may be carried out, for example, at −78° C. to 100° C. for 1 to 24 hours.

The compound (1h) can be produced from the compound (1i), for example, by allowing the compound (1i) to react with water in the presence of a base.

Examples of the base include LDA, NaOAc, MeONa, MeOK, LiOH, NaOH, KOH, $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; halogenated hydrocarbons such as chloroform and dichloromethane; aromatic hydrocarbons such as toluene and xylene; alcohols such as methanol, ethanol, and isopropanol; and water; or a mixed solvent thereof. The reaction may be carried out, for example, at 20° C. to 100° C. for 1 to 24 hours.

The compound (1g) can be produced from the compound (1h), for example, by subjecting the compound (1h) to Curtius rearrangement reaction using an azidation reagent in the presence of a base.

Examples of the azidation reagent include organic azidation reagents such as diphenylphosphoryl azide or bis(p-nitrophenyl)azidophosphonate; and azide salts such as sodium azide.

Examples of the base include organic bases such as TEA, DIPEA, DBU, DBN, DABCO, imidazole, N-methyl imidazole, N,N-dimethyl aniline, pyridine, 2,6-lutidine, DMAP, LDA, lithium hexamethyldisilazide (LHMDS), and sodium bis(trimethylsilyl)amide (NaHMDS); and inorganic bases such as $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; and aromatic hydrocarbons such as toluene and xylene; or a mixed solvent thereof. The reaction may be carried out, for example, at 20° C. to 120° C. for 1 to 24 hours.

The compound (1b) can be produced from the compound (1g), for example, by allowing the compound (1g) to react with water in the presence of a base.

Examples of the base include organic bases such as TEA, DIPEA, DBU, DBN, DABCO, imidazole, N-methyl imidazole, N,N-dimethyl aniline, pyridine, 2,6-lutidine, DMAP, and tetrabutylammonium hydroxide; an inorganic bases such as NaOAc, $Na_2CO_3$, $NaHCO_3$, NaH, $K_2CO_3$, and $Cs_2CO_3$. Examples of the solvent include hydrocarbons such as hexane and heptane; ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; halogenated hydrocarbons such as chloroform and dichloromethane; aromatic hydrocarbons such as toluene and xylene; and water; or a mixed solvent thereof. The reaction may be carried out, for example, at 20° C. to 120° C. for 1 to 24 hours.

The compound (17) can be produced from the isocyanate compound (1g), for example, by allowing the isocyanate compound (1g) to react with a compound having a carboxylic acid in the presence of a Lewis acid or a base under a heating condition.

Examples of the compound having a carboxylic acid include N-protected amino acids such as Fmoc-amino acid-OH. Examples of the Lewis acid include inorganic salts such as magnesium perchlorate. Examples of the base include organic bases such as TEA, DIPEA, DBU, DBN, DABCO, N-methyl imidazole, N,N-dimethyl aniline, pyridine, 2,6-lutidine, and DMAP. Examples of the solvent include ethers such as diethyl ether, diisopropyl ether, CPME, tetrahydrofuran, and dioxane; nitriles such as acetonitrile; ketones such as acetone and methyl ethyl ketone; amides such as DMF, dimethylacetamide, and hexamethylphosphoramide; sulfoxides such as dimethyl sulfoxide; lactams such as N-methylpyrrolidone; halogenated hydrocarbons such as chloroform and dichloromethane; and aromatic hydrocarbons such as toluene and xylene; or a mixed solvent thereof. The reaction may be carried out, for example, at 20° C. to 120° C. for 1 to 24 hours.

The alkyldiphenylmethane compound (1) of the present invention can be used as a protective agent for a functional group such as a carboxy group, a hydroxy group, an amino group, an amide group, or a mercapto group. A compound in which a carboxy group, a hydroxy group, an amino group, an amide group, or a mercapto group is protected with the alkyldiphenylmethane compound (1) of the present invention is characterized by increased liquidity and solubility in a solvent. Thus, a compound in which a functional group is protected with the alkyldiphenylmethane compound (1) of the present invention as a protective agent becomes liquid, and can be separated and purified by an operation such as liquid-liquid phase separation. In addition, a protecting group obtained by using the inventive compound can be easily eliminated by an acid or catalytic reduction.

The compound, which can be protected by the alkyldiphenylmethane compound (1) of the present invention, may be a compound having a carboxy group, a hydroxy group, an amino group, an amide group, or a mercapto group. Examples thereof include amino acids, peptides, saccharides, proteins, nucleotides, various medicinal compounds and agrochemical compounds, various polymers and dendrimers, and others.

Examples of a method for synthesizing peptides using the alkyldiphenylmethane compound (1) of the present invention as a protective agent include a method of production comprising the following steps (1) to (4).

(1) The alkyldiphenylmethane compound (1) of the present invention is condensed with a C terminal carboxy group of an N-protected amino acid or an N-protected peptide in a soluble solvent to give an N- and C-protected amino acid or an N- and C-protected peptide in which the C terminal is protected with the alkyldiphenylmethane compound (1) of the present invention. Alternatively, the alkyldiphenylmethane compound (1) of the present invention is reacted with a C terminal carboxamide group of an N-protected amino acid or an N-protected peptide in a soluble solvent to give an N- and C-protected amino acid or an N- and C-protected peptide in which the C terminal is protected with the alkyldiphenylmethane compound (1) of the present invention.

(2) The protecting group of the N terminal of the resulting N- and C-protected amino acid or N- and C-protected peptide is removed to give a C-protected amino acid or C-protected peptide.

(3) An N-protected amino acid or an N-protected peptide is condensed with the N terminal of the resulting C-protected amino acid or C-protected peptide to give an N- and C-protected peptide.

(4) The protecting group of the N terminal and the protecting group of the C terminal of the resulting N- and C-protected peptide are removed to afford a desired peptide.

EXAMPLES

The present invention is described in more detail with reference to Examples below, but it should not be construed as being limited to the Examples in any way.

Example 1

Synthesis of TIPS2-Dpm(Me)-NCO

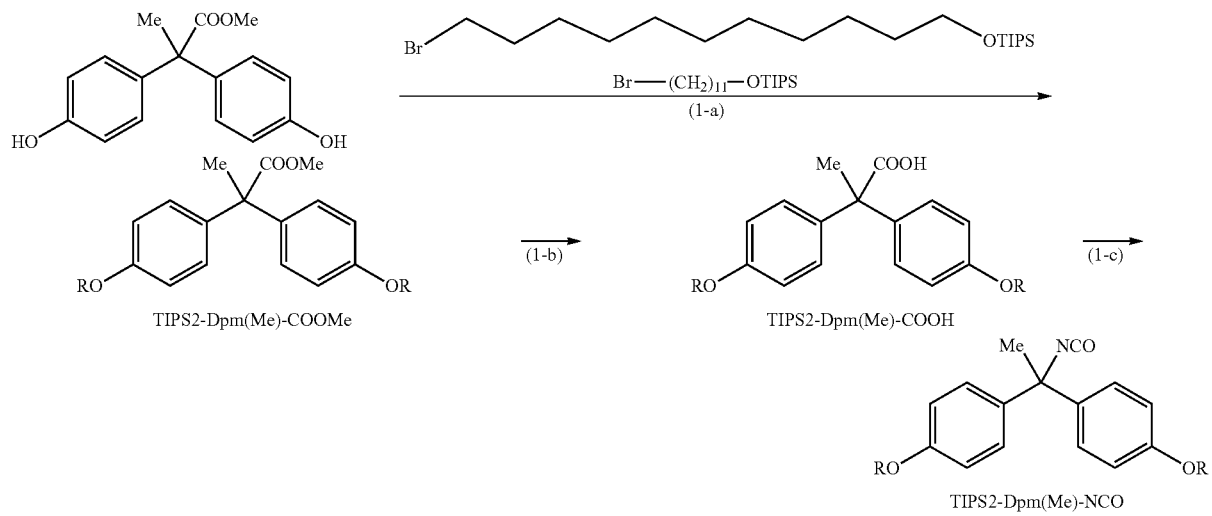

(In the above scheme, R represents —$(CH_2)_{11}$—OTIPS, and TIPS represents triisopropylsilyl. Hereinafter, Br—$(CH_2)_{11}$—OTIPS, TIPS2-Dpm(Me)-COOMe, TIPS2-Dpm(Me)-COOH, and TIPS2-Dpm(Me)-NCO represent the respective structures in the above scheme.)

Reference Example (1-a): TIPS2-Dpm(Me)-COOMe

In 55.0 mL of DMF, 2.50 g of methyl 2,2-bis(4-hydroxyphenyl)propionate (9.20 mmol) and 11.2 g of Br—$(CH_2)_{11}$-OTIPS (2.76 mmol) were dissolved, and then 5.72 g of potassium carbonate (41.4 mmol) was added to the solution, followed by stirring at 90° C. for 3.5 hours. The reaction solution was cooled to room temperature, 200 mL of heptane and 200 mL of water were added to the solution, and the solution was washed by liquid-liquid extraction. The resulting heptane layer was washed by liquid-liquid extraction twice with 50 mL of DMF and twice with 100 mL of water. The heptane layer was concentrated under reduced pressure, and the resulting residue was purified by silica gel chromatography (heptane:ethyl acetate=120:0 to 45:1) to afford 7.15 g of TIPS2-Dpm(Me)-COOMe.

$^1$H-NMR (400 MHz, CDCl$_3$) δ0.99-1.15 (m, 42H), 1.22-1.38 (m, 24H), 1.38-1.48 (m, 4H), 1.48-1.58 (m, 4H), 1.72-1.80 (m, 4H), 1.87 (s, 3H), 3.67 (t, 4H), 3.71 (s, 3H), 3.93 (t, 4H), 6.81 (dt, 4H), 7.11 (dt, 4H)

$^{13}$C-NMR (100 MHz, CDCl$_3$) δ12.1 (12C), 18.2 (6C), 26.0 (2C), 26.2 (2C), 27.5 (2C), 29.5 (2C), 29.6 (4C), 29.7 (4C), 29.8 (2C), 33.2 (2C), 52.5, 55.3, 63.6 (2C), 68.1 (2C), 114.0 (4C), 129.1 (4C), 136.6 (2C), 158.0 (2C), 176.3

ESIMS MNa$^+$ 947.8

Reference Example (1-b): TIPS2-Dpm(Me)-COOH

In 10.0 mL of tetrahydrofuran, 4.63 g of TIPS2-Dpm(Me)-COOMe (5.00 mmol) was dissolved, and then 80.0 mL of isopropanol and 10.0 mL of 5.0 M sodium hydroxide aqueous solution were added to the solution, followed by stirring at 90° C. for 1 hour and then refluxing for 4.5 hours. The reaction solution was cooled to room temperature, and concentrated under reduced pressure. The resulting residue was dissolved in 150 mL of ethyl acetate, and the solution was washed by liquid-liquid extraction once with 150 mL of 1 N hydrochloric acid aqueous solution and twice with 100 mL of water. The organic layer was concentrated under reduced pressure, and the resulting residue was purified by silica gel chromatography (heptane:ethyl acetate=40:1 to 4:1) to afford 3.21 g of TIPS2-Dpm(Me)-COOH.

$^1$H-NMR (400 MHz, CDCl$_3$) δ1.00-1.14 (m, 42H), 1.24-1.38 (m, 24H), 1.38-1.48 (m, 4H), 1.48-1.58 (m, 4H), 1.70-1.80 (m, 4H), 1.87 (s, 3H), 3.67 (t, 4H), 3.93 (t, 4H), 6.82 (dt, 4H), 7.17 (dt, 4H)

$^{13}$C-NMR (100 MHz, CDCl$_3$) δ12.1 (12C), 18.2 (6C), 25.9 (2C), 26.2 (2C), 27.2, 29.4 (2C), 29.5 (2C), 29.6 (2C), 29.7 (4C), 29.8 (2C), 33.2 (2C), 55.1, 63.7 (2C), 68.1 (2C), 114.0 (4C), 129.2 (4C), 136.0 (2C), 158.1 (2C), 180.8

ESIMS MNa$^+$ 933.8

Example (1-c): TIPS2-Dpm(Me)-NCO

In 39.0 mL of toluene, 6.38 g of TIPS2-Dpm(Me)-COOH (7.00 mmol) was dissolved, and then 1.30 mL of triethylamine (9.10 mmol) and 2.00 mL of diphenylphosphoryl azide (9.10 mmol) were added to the solution, followed by stirring at 100° C. for 1 hour. The reaction solution was cooled to room temperature, and concentrated under reduced pressure. The resulting residue was dissolved in 180 mL of heptane, and the solution was washed by liquid-liquid extraction once with 100 mL of acetonitrile, twice with 100 mL of 3% sodium hydrogen carbonate aqueous solution, twice with 100 mL of water, and twice with 50 mL of acetonitrile. The resulting organic layer was concentrated under reduced pressure to afford 6.24 g of TIPS2-Dpm(Me)-NCO.

¹H-NMR (400 MHz, CDCl₃) δ1.00-1.15 (m, 42H), 1.24-1.38 (m, 24H), 1.38-1.48 (m, 4H), 1.48-1.58 (m, 4H), 1.72-1.80 (m, 4H), 2.03 (s, 3H), 3.66 (t, 4H), 3.93 (t, 4H), 6.82 (dt, 4H), 7.23 (dt, 4H)

¹³C-NMR (100 MHz, CDCl₃) δ12.1 (12C), 18.2 (6C), 25.9 (2C), 26.2 (2C), 29.4 (2C), 29.5 (2C), 29.6 (2C), 29.7 (4C), 29.8 (2C), 32.5, 33.2 (2C), 63.6 (2C), 65.5, 68.1 (2C), 114.2 (4C), 124.2, 127.1 (4C), 138.3 (2C), 158.4 (2C)

Example 2

Synthesis of TIPS2-Dpm(Me)-NH₂

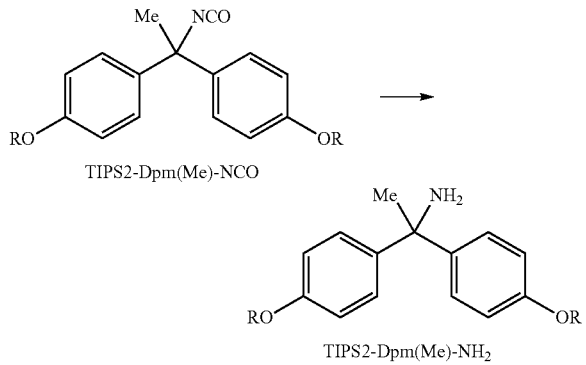

(In the above scheme, R represents —(CH₂)₁₁-OTIPS, and TIPS represents triisopropylsilyl. Hereinafter, TIPS2-Dpm(Me)-NCO and TIPS2-Dpm(Me)-NH₂ represent the respective structures in the above scheme.)

In 12 mL of tetrahydrofuran, 1.82 g of TIPS2-Dpm(Me)-NCO (2.00 mmol) was dissolved, and then 6.0 mL of 10% lithium hydroxide aqueous solution and 30 mL of isopropanol were added to the solution, followed by stirring at 45° C. for 1 hours. Then, 6.0 mL of water was added to the solution, followed by refluxing for 1 hour. The reaction solution was cooled to room temperature, and concentrated under reduced pressure. The resulting residue was dissolved in 120 mL of heptane, 60 mL of ethyl acetate was added to the solution, and the solution was washed by liquid-liquid extraction thrice with 50 mL of water. The organic layer was concentrated under reduced pressure, and the resulting residue was purified by silica gel chromatography (heptane:ethyl acetate:triethylamine=19:1:0.4 to ethyl acetate:triethylamine=50:1) to afford 771 mg of TIPS2-Dpm(Me)-NH₂.

¹H-NMR (400 MHz, CDCl₃) δ1.00-1.14 (m, 42H), 1.25-1.38 (m, 24H), 1.38-1.48 (m, 4H), 1.48-1.58 (m, 4H), 1.78-1.90 (m, 6H), 1.80 (s, 3H), 3.66 (t, 4H), 3.92 (t, 4H), 6.80 (dt, 4H), 7.26 (dt, 4H)

¹³C-NMR (100 MHz, CDCl₃) δ12.2 (12C), 18.2 (6C), 26.0 (2C), 26.2 (2C), 29.5 (2C), 29.6 (4C), 29.7 (4C), 29.8 (2C), 32.4, 33.2 (2C), 57.7, 63.7 (2C), 68.1 (2C), 114.0 (4C), 127.3 (4C), 142.3 (2C), 157.6 (2C)

Example 3

Synthesis of TIPS2-Dpm(Me)-OH

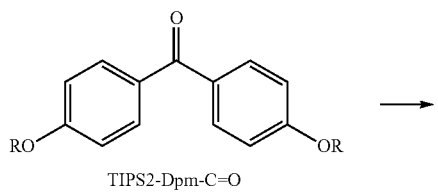

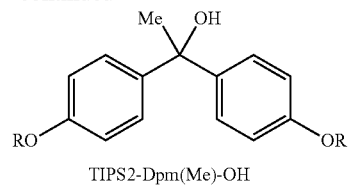

(In the above scheme, R represents —(CH₂)₁₁-OTIPS, and TIPS represents triisopropylsilyl. Hereinafter, TIPS2-Dpm-C=O and TIPS2-Dpm(Me)-OH represent the respective structures in the above scheme.)

In 92.6 mL of anhydrous tetrahydrofuran, 20.82 g of TIPS2-Dpm-C=O (24.0 mmol) was dissolved, and the air in a reaction container was replaced by nitrogen, followed by cooling to 0° C. To the solution, 27.4 mL of 1.4 M methylmagnesium bromide solution (tetrahydrofuran:toluene=1:3) (38.4 mmol) was gradually added, followed by stirring at 40° C. for 2.5 hours. The reaction solution was cooled to 0° C., 300 mL of 5% ammonium chloride aqueous solution was added to the solution. The solution was heated to room temperature, 700 mL of heptane was added to the solution, and the solution was washed by liquid-liquid extraction. The resulting organic layer was washed by liquid-liquid extraction once with 200 mL of water and once with 150 mL of acetonitrile. The organic layer was concentrated under reduced pressure, and the resulting residue was purified by silica gel chromatography (heptane:ethyl acetate=50:1 to 8:1) to afford 16.90 g of TIPS2-Dpm(Me)-OH.

¹H-NMR (400 MHz, Benzene-d₆) δ1.05-1.1.20 (m, 42H), 1.20-1.40 (m, 24H), 1.40-1.49 (m, 4H), 1.56-1.69 (m, 9H), 1.78 (s, 3H), 3.63-3.74 (m, 8H) 6.88 (dt, 4H), 7.39 (dt, 4H)

¹³C-NMR (100 MHz, CDCl₃) δ12.1 (12C), 18.1 (6C), 25.9 (2C), 26.2 (2C), 29.4 (2C), 29.5 (2C), 29.6 (4C), 29.7 (4C), 31.2, 33.1 (2C), 63.6 (2C), 68.0 (2C), 75.8, 114.0 (4C), 127.1 (4C), 140.4 (2C), 158.1 (2C)

ESIMS MNa⁺ 905.7

Example 4

Solubility of Peptide Derivative

Results of measurement of solubility of a peptide protected with an alkyldiphenylmethane protective agent of the present invention are shown below.

Peptide used as model: H-Phe-Leu-Gly-NH₂

H-Phe-Leu-Gly-NH₂ and H-Phe-Leu-Gly-NH-(TIPS2-Dpm(Me)) were synthesized, CPME (cyclopentyl methyl ether) was saturated with each of the compounds at 25° C., and the solubility was measured.

As a result, merely 0.2 mM of H-Phe-Leu-Gly-NH₂ to which an alkyldiphenylmethane protective agent was not bonded was dissolved in CPME. In contrast, 838 mM or more of H-Phe-Leu-Gly-NH-(TIPS2-Dpm(Me)) was dissolved, that is, the peptide derivative led to about 4,190-fold or more increase in solubility. The results demonstrate that solubility of a peptide in an organic solvent is significantly increased by derivatization using the alkyldiphenylmethane protective agent. H-Phe-Leu-Gly-NH₂ and H-Phe-Leu-Gly-NH-(TIPS2-Dpm(Me)) represent the following structures.

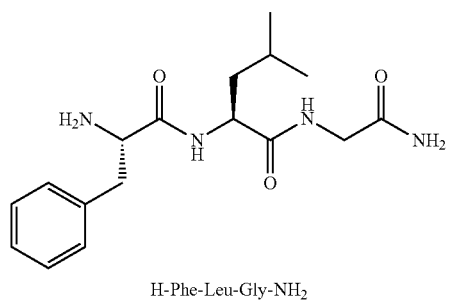

H-Phe-Leu-Gly-NH₂

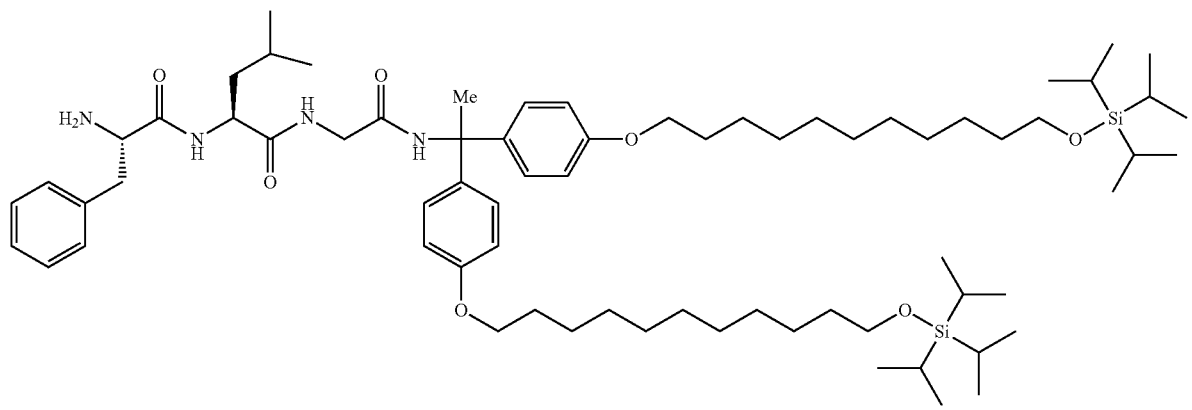

H-Phe-Leu-Gly-NH-(TIPS2-Dpm(Me))

Example (4-a)

Synthesis of H-Phe-Leu-Gly-NH-(TIPS2-Dpm(Me))

In 4.2 mL of CPME, 377 mg of TIPS2-Dpm(Me)-NH₂ (0.43 mmol) was dissolved. To the solution, 1.8 mL of DMF, 364 μL of DIPEA (2.14 mmol), 267 mg of Fmoc-Gly-OH (0.90 mmol), 121 mg of ethyl (hydroxyimino)cyanoacetate (Oxyma) (0.85 mmol), and 366 mg of [(1-cyano-2-ethoxy-2-oxoethylidenaminooxy)dimethylaminomorpholino]carbenium hexafluorophosphate (0.85 mmol) were added, followed by stirring at room temperature for 1 hour. To the reaction solution, 75 mL of heptane was added. The organic layer was washed by liquid-liquid extraction once with 25 mL of 90% acetonitrile aqueous solution and twice with 20 mL of acetonitrile. The organic layer was concentrated under reduced pressure to afford 455 mg of Fmoc-Gly-NH-(TIPS2-Dpm(Me)). Fmoc-Gly-NH-(TIPS2-Dpm(Me)) represents the following structure.

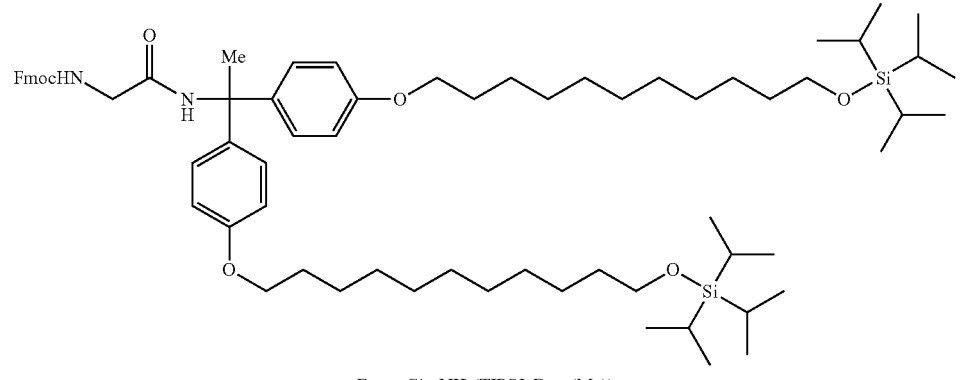

Fmoc-Gly-NH-(TIPS2-Dpm(Me))

¹H-NMR (400 MHz, CDCl₃) δ1.00-1.12 (m, 42H), 1.24-1.38 (m, 24H), 1.38-1.48 (m, 4H), 1.49-1.57 (m, 4H), 1.70-1.80 (m, 4H), 2.15 (s, 3H), 3.66 (t, 4H), 3.84-3.94 (m, 6H), 4.19 (t, 1H), 4.38 (d, 2H), 5.46 (s, 1H), 6.44 (s, 1H), 6.80 (d, 4H), 7.12 (d, 4H), 7.28 (t, 2H), 7.39 (t, 2H), 7.56 (d, 2H), 7.75 (d, 2H)

¹³C-NMR (100 MHz, CDCl₃) δ12.2 (12C), 18.2 (6C), 26.0 (2C), 26.2 (2C), 27.8, 29.4 (2C), 29.6 (4C), 29.7 (4C), 29.8 (2C), 33.2 (2C), 45.3, 47.2, 62.0, 63.7 (2C), 67.4, 68.1 (2C), 114.3 (4C), 120.1 (2C), 125.2 (2C), 127.2 (2C), 127.6 (4C), 127.9 (2C), 137.9 (2C), 141.4 (2C), 143.9 (2C), 156.7, 158.2 (2C), 167.5

ESIMS MNa⁺ 1183.8

In 78.2 mL of CPME, 15.00 g of Fmoc-Gly-NH-(TIPS2-Dpm(Me)) (12.9 mmol) was dissolved. To the solution, 29.3 mL of DMF, 7.9 mL of DIPEA (45.2 mmol), 4.60 g of sodium 3-mercapto-1-propanesulfonate (25.8 mmol) dissolved in 21.5 mL of DMSO, and 6.8 mL of 1,8-diazabicyclo[5.4.0]-7-undecene (DBU) (45.2 mmol) were added, followed by stirring at room temperature for 55 minutes. After observing disappearance of Fmoc-Gly-NH-(TIPS2-Dpm(Me)), the reaction solution was ice cooled, 11.9 mL of 4 M CPME/HCl (47.4 mmol) was added dropwise to the solution. The solution was heated to room temperature, 7.5 mL of CPME, 153 mL of 20% sodium chloride aqueous solution, and 131 mL of 10% sodium carbonate aqueous solution were added to the solution, and the solution was washed by liquid-liquid extraction. To the resulting organic layer, 2.4 mL of DMSO, 2.4 mL of DMF, and 89 mL of 50% dipotassium phosphate aqueous solution were added, and the solution was washed by liquid-liquid extraction to give a mixture containing H-Gly-NH-(TIPS2-Dpm(Me)).

H-Gly-NH-(TIPS2-Dpm(Me)) represents the following structure.

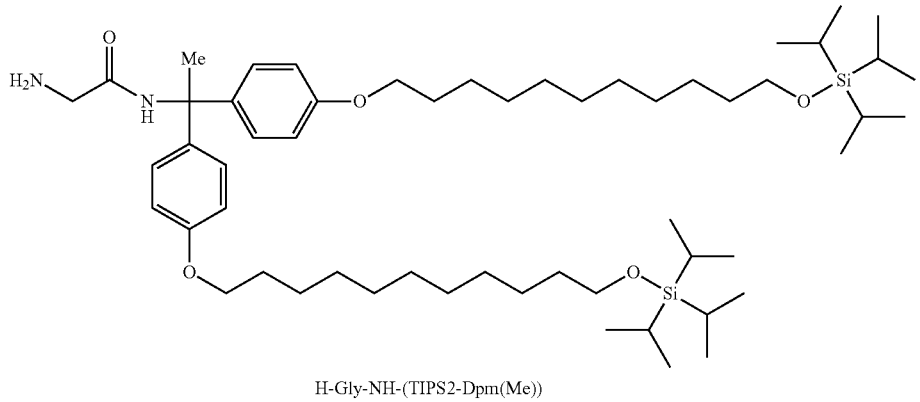 [SMILES: CC(C)[Si](OCCCCCCCCCCCOc1ccc(C(C)(NC(=O)CN)c2ccc(OCCCCCCCCCCCO[Si](C(C)C)(C(C)C)C(C)C)cc2)cc1)(C(C)C)C(C)C ; "H-Gly-NH-(TIPS2-Dpm(Me))"]

H-Gly-NH-(TIPS2-Dpm(Me))

To the resulting mixture, 3.5 mL of CPME, 41.4 mL of DMF, 9.0 mL of DIPEA (51.6 mmol), 5.93 g of Fmoc-Leu-OH (16.8 mmol), 2.20 g of Oxyma (15.5 mmol), and 6.64 g of COMU (15.5 mmol) were added, followed by stirring at room temperature for 25 minutes. After observing disappearance of H-Gly-NH-(TIPS2-Dpm(Me)), 768 µL of 2-(2-aminoethoxy)ethanol (7.75 mmol) was added to the solution, followed by stirring for 15 minutes. To the reaction solution, 5.98 g of 3-mercapto-1-propanesulfonate (33.6 mmol) dissolved in 28.0 mL of DMSO was added, 11.3 mL of DBU (75.5 mmol) and 15.0 mL of DMF were further added, followed by stirring for 55 minutes. After observing disappearance of Fmoc-Leu-Gly-NH-(TIPS2-Dpm(Me)), the reaction solution was ice cooled, 19.8 mL of 4 M CPME/HCl (79.3 mmol) was added dropwise to the solution. The solution was heated to room temperature, 6.1 mL of CPME, 283 mL of 20% sodium chloride aqueous solution, and 177 mL of 10% sodium carbonate aqueous solution were added to the solution, and the solution was washed by liquid-liquid extraction. To the resulting organic layer, 3.4 mL of DMSO, 3.4 mL of DMF, and 128 mL of 50% dipotassium phosphate aqueous solution were added, and the solution was washed by liquid-liquid extraction to give a solution of H-Leu-Gly-NH-(TIPS2-Dpm(Me)).

Fmoc-Leu-Gly-NH-(TIPS2-Dpm(Me)) and H-Leu-Gly-NH-(TIPS2-Dpm(Me)) represent the following structures.

pearance of Fmoc-Phe-Leu-Gly-NH-(TIPS2-Dpm(Me)), the reaction solution was ice cooled, 22.9 mL of 4 M CPME/HCl (91.5 mmol) was added dropwise to the solution. The solution was heated to room temperature, 6.8 mL of CPME, 294 mL of 20% sodium chloride aqueous solution, and 252 mL of 10% sodium carbonate aqueous solution were added to the solution, and the solution was washed by liquid-liquid extraction. To the resulting organic layer, 4.6 mL of DMSO, 4.6 mL of DMF, and 172 mL of 50% dipotassium phosphate aqueous solution were added, and an organic layer was

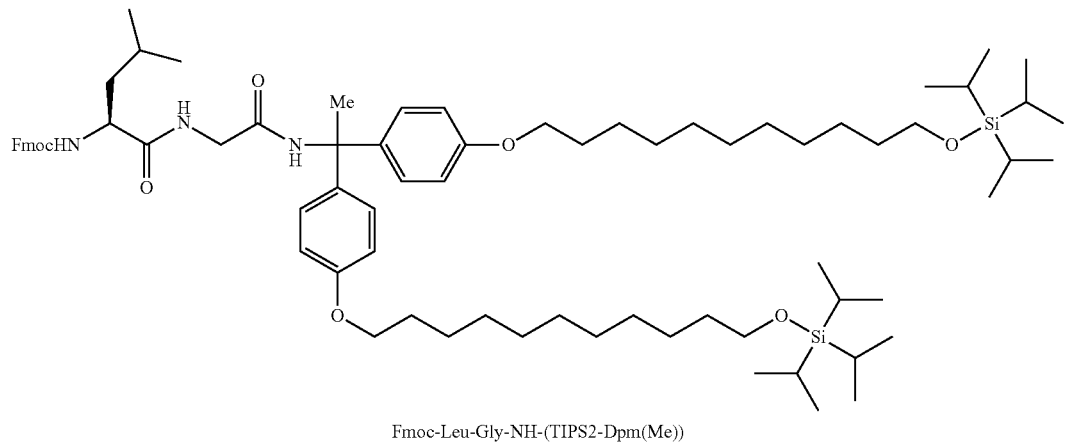

Fmoc-Leu-Gly-NH-(TIPS2-Dpm(Me))

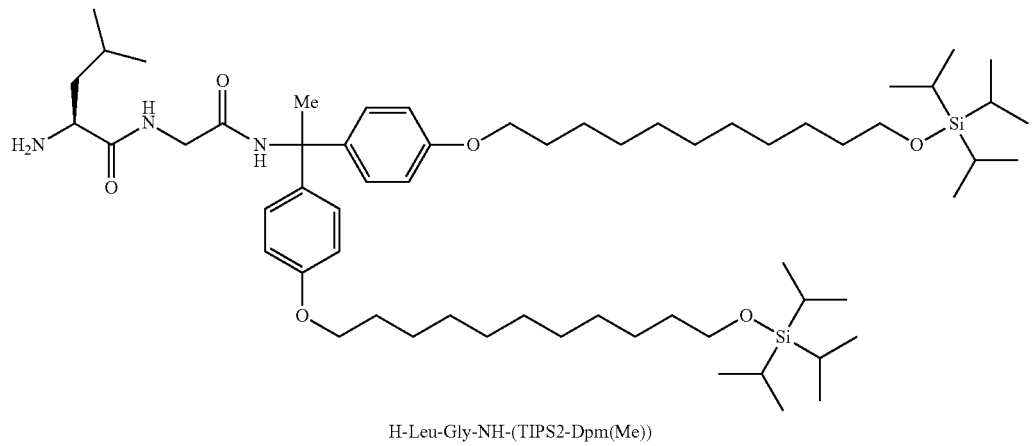

H-Leu-Gly-NH-(TIPS2-Dpm(Me))

To the resulting solution, 12.5 mL of CPME, 58.7 mL of DMF, 9.0 mL of DIPEA (51.6 mmol), 7.50 g of Fmoc-Phe-OH (19.4 mmol), 2.57 g of Oxyma (18.1 mmol), and 7.74 g of COMU (18.1 mmol) were sequentially added, followed by stirring at room temperature for 1 hour and 10 minutes. After observing disappearance of H-Leu-Gly-NH-(TIPS2-Dpm(Me)), 1.28 mL of 2-(2-aminoethoxy)ethanol (12.9 mmol) was added to the solution, followed by stirring for 15 minutes. To the solution, 6.90 g of 3-mercapto-1-propane-sulfonate (38.7 mmol) dissolved in 32.3 mL of DMSO was added, 13.0 mL of DBU (87.1 mmol) was further added, followed by stirring for 40 minutes. After observing disapseparated. The resulting organic layer was concentrated under reduced pressure. The resulting residue was dissolved in 650 mL of heptane, and the solution was washed four times with 150 mL of acetonitrile. The heptane solution was concentrated under reduced pressure, and the resulting residue was purified by silica gel chromatography (heptane: ethyl acetate=2:1 to ethyl acetate) to afford 9.65 g of H-Phe-Leu-Gly-NH-(TIPS2-Dpm(Me)).

ESIMS MNa$^+$ 1222.0

Fmoc-Phe-Leu-Gly-NH-(TIPS2-Dpm(Me)) represents the following structure.

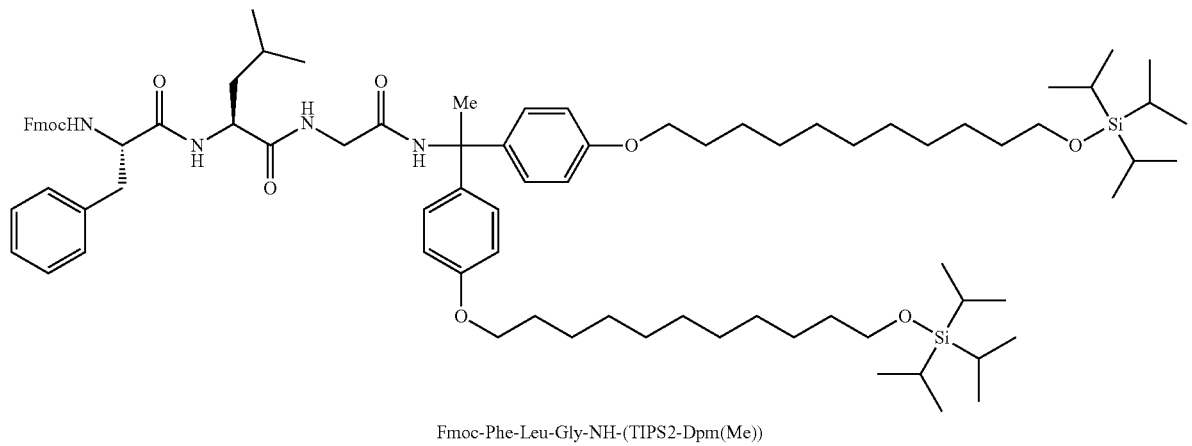

Fmoc-Phe-Leu-Gly-NH-(TIPS2-Dpm(Me))

Example (4-b)

Synthesis of H-Phe-Leu-Gly-NH$_2$

To a mixture of 7.0 mL of dichloromethane, 0.8 mL of TFA (10.5 mmol), and 0.2 mL of triisopropylsilane (0.98 mmol), 240 mg of H-Phe-Leu-Gly-NH-(TIPS2-Dpm(Me)) (0.20 mmol) was added, followed by stirring at room temperature for 45 minutes. After observing disappearance of H-Phe-Leu-Gly-NH-(TIPS2-Dpm(Me)), the reaction solution was concentrated under reduced pressure. The residue was added dropwise to a mixture of 10 mL of heptane and 10 mL of isopropyl ether, and the resulting precipitate was filtered. The precipitate was suspended in a mixture of 10 mL of heptane and 10 mL of isopropyl ether, and the resulting precipitate was filtered. The precipitate was dried to afford 91 mg of H-Phe-Leu-Gly-NH$_2$.

ESIMS MH$^+$ 335.2

The above results demonstrate that solubility in an organic solvent of a compound in which a functional group is protected using an alkyldiphenylmethane protective agent of the present invention is significantly increased.

The invention claimed is:

1. An alkyldiphenylmethane compound represented by general formula (1):

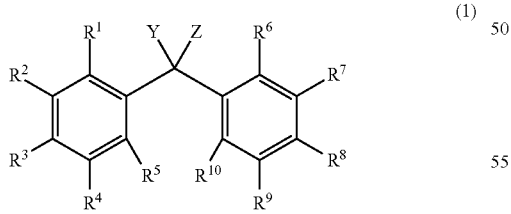

(1)

wherein, Y represents —OR$^{19}$ (wherein R$^9$ represents a hydrogen atom or an active ester-type protecting group), —NHR$^{20}$ (wherein R$^{20}$ represents a hydrogen atom, a C$_{1-6}$ linear or branched alkyl group, or an aralkyl group), an isocyanate group, an azide group, or a halogen atom, Z represents a C$_{1-4}$ linear or branched alkyl group, an alkenyl group, or a cycloalkyl group, at least one of R$^1$ to R$^{10}$ represents a group represented by formula (2):

—O—R$^{11}$—X—A  (2)

and the others each independently represent a hydrogen atom, a halogen atom, a C$_{1-4}$ alkyl group, or a C$_{1-4}$ alkoxy group; R$^{11}$ represents a C$_{1-16}$ linear or branched alkylene group; X represents O or CONR$^{21}$ (wherein R$^{21}$ represents a hydrogen atom or a C$_{1-4}$ alkyl group); and A represents a group represented by formula (3), (4), (5), (6), (7), (8), (9), (10), (11), (12), or (13):

(3)

(4)

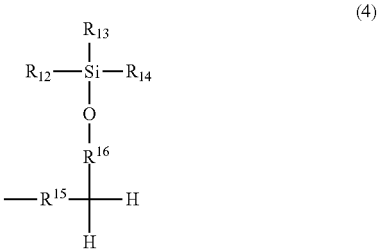

(5)

(6) 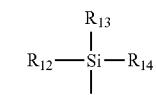

(7) 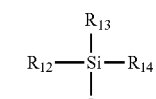

(8) 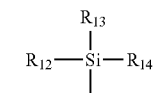

(9) 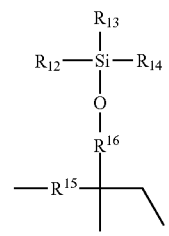

(10) 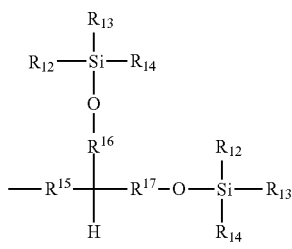

(11) 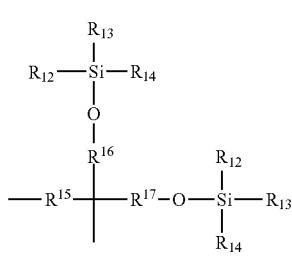

(12) 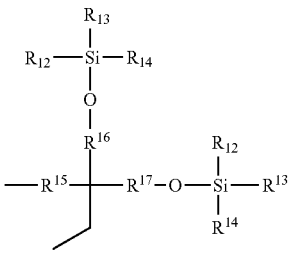

(13) 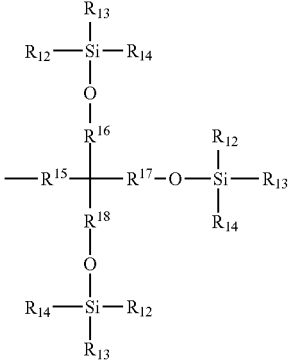

wherein $R^{12}$, $R^{13}$, and $R^{14}$ may be the same or different and each independently represent a $C_{1-6}$ linear or branched alkyl group or an optionally substituted aryl group; $R^{15}$ represents a single bond or a $C_{1-3}$ linear or branched alkylene group; and $R^{16}$, $R^{17}$, and $R^{18}$ each independently represent a $C_{1-3}$ linear or branched alkylene group.

2. The alkyldiphenylmethane compound according to claim 1, wherein Y is —$OR^{19}$ (wherein $R^{19}$ represents a hydrogen atom), —$NHR^{20}$ (wherein $R^{20}$ represents a hydrogen atom, a $C_{1-6}$ linear or branched alkyl group, or an aralkyl group), or an isocyanate group.

3. The alkyldiphenylmethane compound according to claim 1, wherein Z is a $C_{1-4}$ linear or branched alkyl group.

4. The alkyldiphenylmethane compound according to claim 1 wherein at least one of $R^1$ to $R^5$ and at least one of $R^6$ to $R^{10}$ are each independently a group represented by formula (2), and the others are each independently a hydrogen atom, a $C_{1-4}$ alkyl group, or a $C_{1-4}$ alkoxy group.

5. The alkyldiphenylmethane compound according to claim 1 wherein $R^{11}$ is a $C_{2-16}$ linear or branched alkylene group.

6. The alkyldiphenylmethane compound according to claim 1 wherein $R^{11}$ is a $C_{6-16}$ linear or branched alkylene group.

7. The alkyldiphenylmethane compound according to claim 1, wherein $R^{15}$ is a single bond or a methylene group, and $R^{16}$, $R^{17}$, and $R^{18}$ are each independently a methylene group.

8. A method of protecting at least one of a carboxy group, a hydroxy group, an amino group, an amide group, or a mercapto group on a compound which comprises reacting the group with a compound of claim 1.

9. The method of claim 8 wherein the compound having at least one member comprising a carboxy group, a hydroxy group, an amino group, an amide group, or a mercapto group is at least one compound selected from the group consisting of amino acids, peptides, saccharides, proteins, nucleotides.

10. The method of claim 9 the compound is a peptide.

* * * * *